United States Patent
Komori et al.

(10) Patent No.: US 9,337,671 B2
(45) Date of Patent: May 10, 2016

(54) PROTECTIVE ELEMENT, PROTECTIVE ELEMENT FABRICATION METHOD, AND BATTERY MODULE IN WHICH PROTECTIVE ELEMENT IS EMBEDDED

(71) Applicant: Dexerials Corporation, Tokyo (JP)

(72) Inventors: Chisato Komori, Tochigi (JP); Yuji Furuuchi, Tochigi (JP); Yoshihiro Yoneda, Tochigi (JP); Koichi Mukai, Tochigi (JP); Koji Ejima, Tochigi (JP); Takashi Fujihata, Tochigi (JP); Kazutaka Furuta, Tochigi (JP); Toshiaki Araki, Tochigi (JP)

(73) Assignee: Dexerials Corporation, Tokyo (JP)

( * ) Notice: Subject to any disclaimer, the term of this patent is extended or adjusted under 35 U.S.C. 154(b) by 164 days.

(21) Appl. No.: 14/366,630

(22) PCT Filed: Dec. 17, 2012

(86) PCT No.: PCT/JP2012/082684
§ 371 (c)(1),
(2) Date: Jun. 18, 2014

(87) PCT Pub. No.: WO2013/094565
PCT Pub. Date: Jun. 27, 2013

(65) Prior Publication Data
US 2014/0340046 A1    Nov. 20, 2014

(30) Foreign Application Priority Data

Dec. 19, 2011 (JP) .............................. P2011-277123
Dec. 17, 2012 (JP) .............................. P2012-274222

(51) Int. Cl.
*H02J 7/00* (2006.01)
*G01N 27/416* (2006.01)
(Continued)

(52) U.S. Cl.
CPC .......... *H02J 7/0029* (2013.01); *H01H 85/0241* (2013.01); *H01M 2/34* (2013.01);
(Continued)

(58) Field of Classification Search
CPC ......... H02J 7/00; H02J 7/0029; H02J 7/0031;
H02J 7/0007; H02J 2007/0037; H02J 2007/004; G01N 27/416; G01N 27/02; G08B 21/00; H01M 2/34; H01M 10/0525; H01M 2200/103; H01H 85/0241; H01H 69/022; H02H 3/08; H02H 7/18; H02H 9/041; H02H 9/042; Y10T 29/49208
USPC .............. 320/134; 324/434, 441; 340/636.17, 340/638
See application file for complete search history.

(56) References Cited

U.S. PATENT DOCUMENTS 3,600,650 A * 8/1971 Obenhaus ............... H01L 21/00
257/467
4,078,880 A * 3/1978 Hunziker ............... F23N 5/003
324/717
(Continued)

FOREIGN PATENT DOCUMENTS

JP          7-153367 A       6/1995
JP       2001-325869 A      11/2001
(Continued)

OTHER PUBLICATIONS

International Search Report issued in PCT/JP2012/082684 mailed on Jan. 22, 2013 (4 pages).

*Primary Examiner* — Phallaka Kik
(74) *Attorney, Agent, or Firm* — Osha Liang LLP

(57) ABSTRACT

A protective element including a substrate having a first insulating member and a concave portion formed thereon, a heating body layered on the concave portion of the substrate, a second insulating member layered on the substrate so as to cover at least covering the heating body, first and second electrodes layered on a surface of the substrate on which the second insulating member is layered, a heating body electrode layered on the second insulating member so as to be superimposed with the heating body, and electrically connected to a current path between the first and the second electrodes as well as onto and the heating body, and a low-melting point metal layered from the heating body electrode toward the first and the second electrodes configured to cause a blowout of the current path between the first and the second electrodes by heating.

8 Claims, 10 Drawing Sheets

(51) Int. Cl.
*G08B 21/00* (2006.01)
*G01N 27/02* (2006.01)
*H01M 2/34* (2006.01)
*H02H 3/08* (2006.01)
*H01H 85/02* (2006.01)
*H02H 7/18* (2006.01)
*H02H 9/04* (2006.01)
*H01M 10/0525* (2010.01)
*H01H 69/02* (2006.01)

(52) U.S. Cl.
CPC ................ *H02H 3/08* (2013.01); *H02H 7/18* (2013.01); *H02H 9/041* (2013.01); *H02H 9/042* (2013.01); *H02J 7/007* (2013.01); *H02J 7/0031* (2013.01); *G01N 27/416* (2013.01); *G08B 21/00* (2013.01); *H01H 69/022* (2013.01); *H01M 10/0525* (2013.01); *H01M 2200/103* (2013.01); *H02J 2007/004* (2013.01); *H02J 2007/0037* (2013.01); *Y10T 29/49208* (2015.01)

(56) References Cited

U.S. PATENT DOCUMENTS

| | | | | |
|---|---|---|---|---|
| 4,822,983 | A * | 4/1989 | Bremner | H05B 3/56 219/212 |
| 6,909,180 | B2 * | 6/2005 | Ono | H01L 21/563 257/734 |
| 9,214,703 | B2 * | 12/2015 | Ikeda | H01M 10/0431 |
| 2003/0146092 | A1 * | 8/2003 | Heimann | G01N 27/4071 204/424 |
| 2007/0278098 | A1 * | 12/2007 | Yokosawa | G01N 27/4141 204/431 |
| 2013/0122345 | A1 * | 5/2013 | Sato | H01M 2/202 429/121 |

FOREIGN PATENT DOCUMENTS

| | | |
|---|---|---|
| JP | 2004-214033 A | 7/2004 |
| JP | 2006-109596 A | 4/2006 |
| JP | 2008-029167 A | 2/2008 |
| JP | 2011-222264 A | 11/2011 |
| JP | 2011-228199 A | 11/2011 |

\* cited by examiner

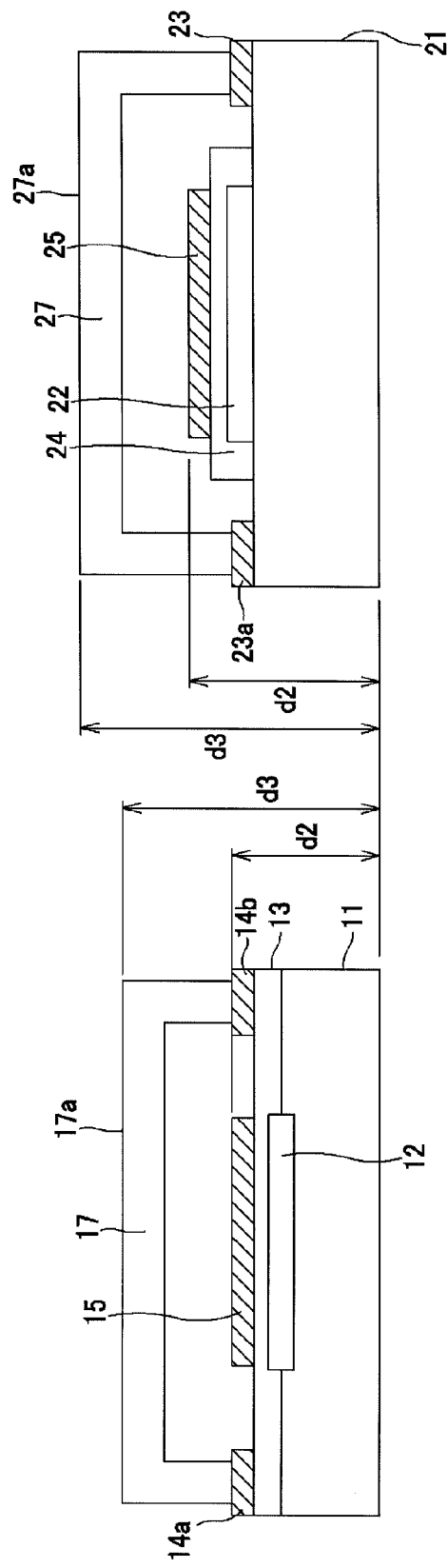

PROTECTIVE ELEMENT, PROTECTIVE ELEMENT FABRICATION METHOD, AND BATTERY MODULE IN WHICH PROTECTIVE ELEMENT IS EMBEDDED

CROSS-REFERENCE TO RELATED APPLICATIONS

This application is a National Stage application of International Patent Application No. PCT/JP2012/082684, filed on Dec. 17, 2012, and claims priority pursuant to 35 U.S.C. §119(a) to Japanese Patent Application No. P2011-277123, filed on Dec. 19, 2011, and Japanese Patent Application No. P2012-274222, filed on Dec. 17, 2012. The international application and priority applications are hereby incorporated by reference in their entirety.

BACKGROUND OF INVENTION

1. Field of the Invention

One or more embodiments of the present invention relate to a protective element that protects a circuit connected onto a current path by causing a blowout to the current path, a method for manufacturing such a protective element, and a battery module in which the protective element is embedded.

2. Background Art

In general, a charging and discharging circuit for a secondary battery, such as a lithium ion battery or the like, has a function for shutting down an output of the battery by activating many protective circuits (Patent Document 1).

In the case when this charging and discharging circuit is normally operated, the output is turned ON/OFF by using an FET transistor; however, because an instantaneous heavy current, such as typically represented by a lightening surge, tends to exceed the operation time of the FET transistor, a protective circuit such as a fuse for detecting an overcurrent to cause a shutdown is used as a protective circuit from the viewpoint of protecting inner circuits. Moreover, an FET is used so as to monitor the state of a battery and shut down the output of the battery, when an abnormal state, such as an overcharge, an overdischarge, heat generation or the like of the battery, is detected.

Moreover, as described in Patent Document 2, the safety of a secondary battery is ensured by using multiple protective circuits having a protective element that compulsorily shuts down a charging operation to a buttery, in the case when, upon charging a secondary battery, a detection of an overcharge to the battery, an abnormal temperature rise of the battery, an erroneous operation due to heat generation of the FET occurs.

Moreover, as described in Patent Document 3, as a protective element for a protective circuit for such a lithium ion secondary battery, a structure has been generally known in which a heating body is formed in the protective element, and by using this heating body, a low-melting point metal on a current path is blown out.

RELATED ART

Patent Document

PTL 1: Japanese Patent Application Laid-Open No. 2008-29167

PTL 2: Japanese Patent Application Laid-Open No. 2006-109596

PTL 3: Japanese Patent Application Laid-Open (Tokkai-Hei) No. 7-153367

For example, by the appearance of a slate-type information terminal or the like, it may be advantageous to make an electronic apparatus including multiple protections thinner.

In the protective element as described in the above-mentioned Patent Document 3, a structure is adopted in which a heating body and a low-melting point metal are thermally connected to each other, with an insulating member interposed therebetween.

In the structure of a conventional protective element, a heating body, an insulating layer and an electrode for connecting a low-melting point metal need to be layered on a substrate. Then, a low-melting point metal is connected to the upper portion of this electrode, and further, on its upper portion, a cap, an inner protective plate or the like for protecting the inside of the element need to be installed, with the result that the entire thickness of a product tends to be increased.

Furthermore, because a comparative large protruding portion is formed on a gap between electrodes to which the low-melting point metal is connected, upon heating the low-melting point metal to be allowed to flow, the flux is interrupted that may cause a longer period of time for a blowout.

SUMMARY OF INVENTION

Accordingly, one or more embodiments of the present invention provide a protective element with which, while providing a reduced height, a reliable blowout of a low-melting point metal upon a current path by heat of a heating body is carried out, and a method for manufacturing such a protective element, and a battery module in which such a protective element is embedded.

A protective element according to one or more embodiments of the present invention may comprise a substrate composed of a first insulating member with a concave portion formed thereon, a heating body layered on the concave portion of the substrate, a second insulating member layered on the substrate so as to cover at least the heating body, first and second electrodes layered on a surface of the substrate on which the second insulating member is layered, a heating body electrode layered on the second insulating member so as to be superimposed with the heating body, and electrically connected onto a current path between the first and second electrodes as well as onto the heating body, and a low-melting point metal that is layered from the heating body electrode toward the first and second electrodes to cause a blowout of a current path between the first electrode and the second electrode by heating, and in this structure, the heating body electrode is disposed at a position specified in the thickness direction of the substrate that is the same position or a lower position relative to the first electrode and the second electrode.

Moreover, a method for manufacturing a protective element according to one or more embodiments of the present invention may comprise stacking a heating body in a concave portion of a substrate made of a first insulating member on which the concave portion is formed; stacking a second insulating member on the substrate so as to cover at least the heating body; stacking first and second electrodes on a surface of the substrate on which the second insulating member is stacked; stacking a heating body electrode electrically connected onto a current path between the first and second electrodes as well as onto the heating body on the second insulating member so as to be superimposed with the heating body; and stacking a low-melting point metal by which the current path between the first electrode and the second electrode is blown out by heating from the heating body electrode over to the first and second electrodes, and in this method, the heating body electrode is disposed at a position specified in the thickness direction of the substrate that is the same position or a lower position relative to the first electrode and the second electrode.

Moreover, a battery module according to one or more embodiments of the present invention may comprise a battery composed of one or more chargeable and dischargeable battery cells, a charging and discharging control circuit that is connected to the battery in series with each other so as to control charging and discharging processes of the battery, a protective element connected onto a charging and discharging current path between the battery and the charging and discharging control circuit, a detection circuit for detecting a voltage value of each of the battery cells of the battery, and a current control element for controlling an electric current flowing through the protective element, and in this structure, the protective element is provided with: a substrate composed of a first insulating member with a concave portion formed thereon, a heating body on the concave portion of the substrate, a second insulating member layered on the substrate so as to cover at least the heating body, first and second electrodes layered on a surface of the substrate on which the second insulating member is layered, and connected onto the charging and discharging current path, a heating body electrode layered on the second insulating member so as to be superimposed with the heating body, and electrically connected onto a current path between the first and second electrodes as well as onto the heating body, and a low-melting point metal that is layered from the heating body electrode toward the first and second electrodes to cause a blowout of a current path between the first electrode and the second electrode by heating, and in this structure, the heating body electrode is disposed at a position specified in the thickness direction of the substrate that is the same position or a lower position relative to the first electrode and the second electrode, and the current control element carries out a controlling process such that when a voltage value of each of the battery cells detected by the detection circuit is located out of a predetermined range, a current is allowed to flow from a heating body electrode to a heating body.

Moreover, a protective element according to one or more embodiments of the present invention may comprise a substrate composed of an insulating member, first and second electrodes layered on a surface of the substrate, a substrate electrode layered between the first and second electrodes on the surface of the substrate, a low-melting point metal that is layered from the substrate electrode toward the first and second electrodes to cause a blowout of a current path between the first electrode and the second electrode by heating, a cap covering the surface of the substrate, a heating body formed on a ceiling surface portion of the cap; and a heating body electrode layered on the surface of the substrate, and electrically connected to the heating body through a conductive layer formed on the cap, and in this structure, the substrate electrode is disposed at a position specified in the thickness direction of the substrate that is the same position or a lower position relative to the first electrode and the second electrode.

Furthermore, a battery module according to one or more embodiments of the present invention may comprise a battery composed of one or more chargeable and dischargeable battery cells, a charging and discharging control circuit that is connected to the battery in series with each other so as to control charging and discharging processes of the battery, a protective element connected onto a charging and discharging current path between the battery and the charging and discharging control circuit, a detection circuit for detecting a voltage value of each of the battery cells of the battery, and a current control element for controlling an electric current flowing through the protective element, and in this structure, the protective element is provided with: a substrate composed of an insulating member, first and second electrodes formed on a surface of the substrate, a substrate electrode layered between the first and second electrodes on the surface of the substrate, a low-melting point metal that is layered from the substrate electrode toward the first and second electrodes to cause a blowout of a current path between the first electrode and the second electrode by heating, a cap covering a surface of the substrate, a heating body formed on a ceiling surface portion of the cap, a heating body electrode layered on the surface of the substrate and electrically connected to the heating body through a conductor layer formed on the cap, and in this structure, the substrate electrode is disposed at a position specified in the thickness direction of the substrate that is the same position or a lower position relative to the first electrode and the second electrode, and the current control element carries out a controlling process such that when a voltage value of each of the battery cells detected by the detection circuit is located out of a predetermined range, a current is allowed to flow from the heating body electrode to the heating body.

In one or more embodiments of the present invention, because the heating body is sandwiched between a substrate made of a first insulating member and a second insulating member, the positions of the heating body and a low-melting point metal can be adjusted with high precision in accordance with the thickness of the second insulating member, and because a heating body electrode positioned at a current path between the first and second electrodes is prevented from protruding relative to the first electrode and the second electrode, the low-melting point metal is not formed into a convex shape, so that when heated and allowed to flow, its flux is not interrupted. Therefore, one or more embodiments of the present invention may make it possible to positively achieve a reliable blowout of the low-melting metal on a current path by heat of the heating body, while implementing a reduced height.

BRIEF DESCRIPTION OF DRAWINGS

FIG. 7(A) and FIG. 7(B) are views for evaluating a product entire thickness in the protective element as well as a protective element and a comparative example according to one or more embodiments of the present invention.

DETAILED DESCRIPTION

In embodiments of the invention, numerous specific details are set forth in order to provide a more thorough understanding of the invention. However, it will be apparent to one with ordinary skill in the art that the invention may be practiced without these specific details. In other instances, well-known features have not been described in detail to avoid obscuring the invention. Referring to FIGS., the following description will discuss embodiments for carrying out one or more embodiments of the present invention in detail. Additionally, the present invention is not intended to be limited only by the following embodiments, and various modifications may be made therein without departing from the scope of one or more embodiments of the present invention.

Figure 1:
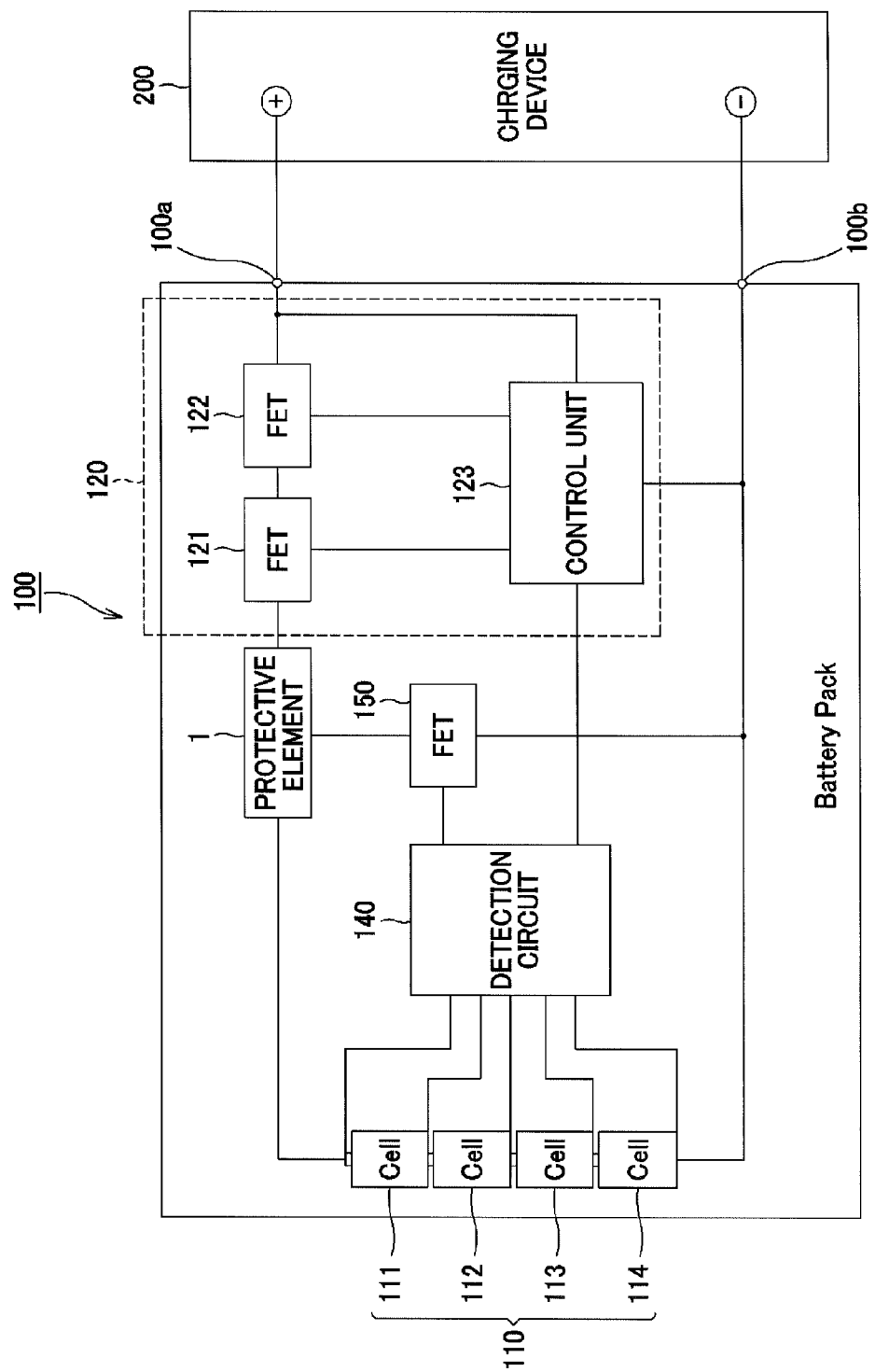
FIG. 1 is a view showing an overall configuration of a battery module, in which a protective element is embedded according to one or more embodiments of the present invention.

A protective element according to one or more embodiments of the present invention may include a circuit embedded in a battery composed of chargeable and dischargeable battery cells and a charging and discharging control circuit, which is embedded and used in a battery module 100 having a battery 110 that may comprise at least four chargeable and dischargeable battery cells 111 to 114, for example, shown in FIG. 1.

That is, in one or more embodiments, the battery module 100 has the battery 110, a charging and discharging control circuit 120 for controlling charging and discharging processes of the battery 110, a protective element 1 to protect the battery 110 and the charging and discharging control circuit 120, a detection circuit 140 for detecting a voltage of each of the battery cells 111 to 114, and a current control element 150 for controlling operations of the protective element 1 in accordance with the detection results of the detection circuit 140.

As described above, the battery 110 may comprise battery cells 111 to 114, such as, for example, lithium ion batteries, which may be connected in series to one another and may require controlling processes so as not to cause an overcharged state or an overdischarged state, and is removably connected to a charging device 200 so that a charging voltage is applied thereto from a charging device 200 through a positive electrode terminal 100a and a negative electrode terminal 100b of the battery module 100.

The charging and discharging control circuit 120 is provided with two current control elements 121, 122 that are series connected onto a current path, with an electric current flowing from the battery 110 to the charging device 200, and a control unit 123 for controlling operations of these current control elements 121, 122. Each of the current control elements 121, 122 may comprise, for example, field-effect transistors (hereinafter, referred to as "FET"), and controls conduction and blowout of the current path of the battery 110 by a gate voltage controlled by the control unit 123. The control unit 123 is operated upon receipt of a power supply from the charging device 200, and in the case when based upon the result of detection by the detection circuit 140, the battery 110 is in an overdischarged or overcharged state, controls the operation of the current control element 121, 122 so as to cause a blowout of the current path.

The protective element 1 is connected onto, for example, a charging and discharging current path between the battery 110 and the charging and discharging control circuit 120, and its operations are controlled by the current control element 150.

The detection circuit 140 is connected to the respective battery cells 111 to 114, and detects a voltage value of each of the battery cells 111 to 114 so that the detected voltage value is supplied to the control unit 123 of the charging and discharging control circuit 120. Moreover, in the case when any one of the battery cells 111 to 114 causes an overcharging voltage or an overdischarging voltage, the detection circuit 140 releases a control signal for controlling the current control element 150.

In the case when the detection signal released from the detection circuit 140 shows that the voltage value of any one of the battery cells 111 to 114 is located out of a predetermined range, that is, more specifically, has caused an overcharged or overdischarged state, the current control element 150 operates the protective element 1 to cause a blowout of the charging and discharging current path of the battery 110.

In the battery module 100 configured as described above, the following description will discuss the configuration of the protective element 1 in detail.

Figure 2:
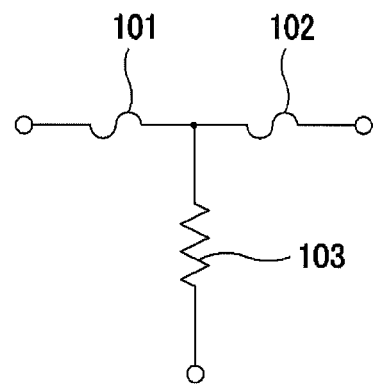
FIG. 2 is a view showing a circuit configuration of a protective element according to one or more embodiments of the present invention.

First, according to one or more embodiments of the present invention, the protective element 1 is provided with a circuit configuration, for example, shown in FIG. 2. That is, the protective element 1 has the circuit configuration composed of fuses 101, 102 connected in series with each other, and a resistor 103 that melts the fuses 101, 102 when energized through a contact point between the fuses 101, 102. Moreover, in the protective element 1, for example, the fuses 101, 102 are connected onto the charging and discharging current path, with the resistor 103 being connected to the current control element 150.

The protective element 1 having the above-mentioned circuit configuration may provide a reliable blowout of a low-melting metal on a current path by heat of a heating body as well as a reduced height, for example, by a structural body 1a, shown in FIG. 3.

Figure 3A:
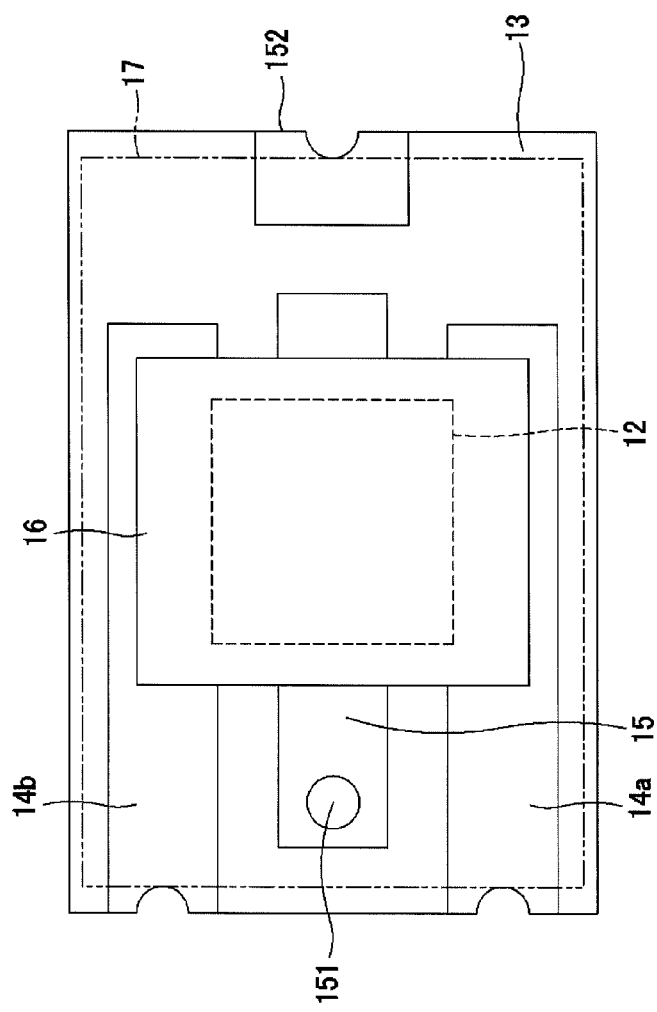
FIG. 3(A) and FIG. 3(B) are views for describing a specific structure of the protective element according to one or more embodiments of the present invention.
Figure 3B:
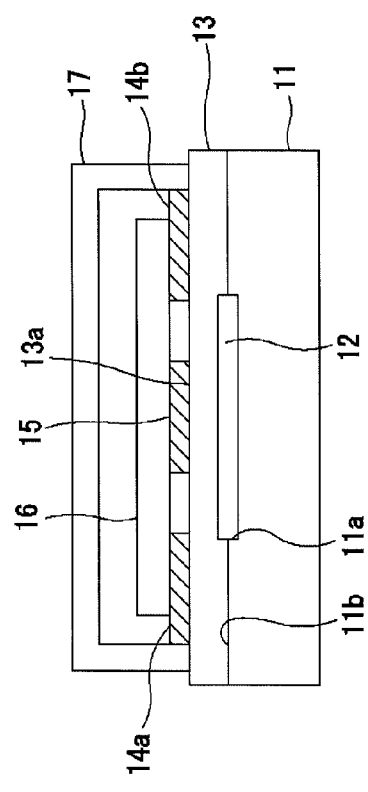

In this case, FIG. 3(A) is a cross-sectional view seen from the XY plane of the structural body 1a disposed based upon the XYZ axes of three-dimensional orthogonal coordinates. Moreover, FIG. 3(B) is a view for describing a layered structure of the structural body 1a seen from the XZ plane.

The structural body 1a is configured by stacking the following members on a rectangular-shaped substrate 11 made of a first insulating member on which a concave portion 11a is formed. In this case, the first insulating member is a member having an insulating property, for example, including alumina, glass ceramics, mullite, zirconia or the like.

First, on the substrate 11, a heating body 12 functioning as the above-mentioned resistor 103 is layered on the concave portion 11a formed in the center thereof. In this case, the heating body 12 is a conductive member having a comparatively high resistance value, made of, for example, W, Mo, Ru or the like, which generates heat when energized.

Subsequently, a second substrate 13 serving as a second insulating member is layered thereon in a manner so as to cover the entire surface 11b of the substrate 11 including the concave portion 11a in which the heating body 12 is layered. In this case, in the same manner as in the first insulating member, the second insulating member is a member having an insulating property, for example, including alumina, glass ceramics, mullite, zirconia or the like.

Additionally, the second substrate 13 may be formed by using, for example, a ceramic substrate of a film shape or a sheet shape, or by coating the surface 11b with a pasty insulating material. From the viewpoint of preventing the generation of pinholes and subsequent degradation in the insulating property, when the second substrate 13 is made thinner, in particular, a ceramic substrate in a film shape may be adopted as the second substrate 13.

Moreover, to obtain a blowout characteristic with respect to the low-melting point metal 16 to be described later, the second substrate 13 made of the second insulating member may be prepared as a member having a higher thermal conductivity than that of the substrate 11 made of the first insulating member. For example, in the case when a glass ceramic material having a thermal conductivity of 1.9 to 2.2 is used as the first insulating member of the substrate 11, a dielectric paste having a thermal conductivity of 2.5 to 3.5 as the insulating material for the second substrate 13 may be used.

Subsequently, above a surface 11b of the substrate 11 on which the second substrate 13 is layered, a first electrode 14a and a second electrode 14b are layered. In this case, the first electrode 14a and the second electrode 14b are made of, for example, W, MoAg, Pt, Pd, Sn, Au, Cu or the like, and when embedded in the aforementioned charging and discharging control circuit 120, these are connected onto the charging and discharging current path.

Subsequently, on the upper surface 13a of the second substrate 13 on which the heating body 12 is superimposed, a heating body electrode 15 is layered. In this case, the heating body electrode 15 is made of, for example, W, Mo, Ag, Pt, Pd, Sn, Au, Cu or the like, and prepared as an electrode that is electrically connected onto a current path between the first electrode 14a and the second electrode 14b as well as onto the heating body 12. Moreover, the heating body electrode 15 is disposed at a position having the same height as that of the first electrode 14a and the second electrode 14b, with the height in the thickness direction of the substrate 11, that is, with the height in the z-axis direction.

Next, over an area from the heating body electrode 15 to the first electrode 14a and the second electrode 14b, a low-melting point metal 16 is layered. In this case, the low-melting point metal 16 is a member corresponding to the above-mentioned fuses 101, 102, and made of, for example, In, Ag, Sn, Pb, Au or the like, which functions as a blowout of the current path between the first electrode 14a and the second electrode 14b by heating.

Moreover, after the low-melting point metal 16 has been layered, a cap 17 is disposed so as to cover the low-melting point metal 16.

Additionally, as shown in FIG. 3(A), in the structural body 1a, the heating body electrode 15 is electrically connected to the heating body 12 through a through hole 151 formed in the thickness direction of the substrate 11. Moreover, the heating body 12 is electrically connected to a connection terminal 152, and as described earlier, is further electrically connected to the current control element 150, for example, through this connection terminal 152.

The protective element 1 relating to the structural body 1a formed as described above is configured such that the heating body 12 is sandwiched between the substrate 11 and the second substrate 13, with the height in the thickness direction of the substrate 11 in the heating body electrode 15 being set to the same height as the first electrode 14a and the second electrode 14b.

In this manner, the protective element 1 relating to the structural body 1a can adjust the positions of the heating body 12 and the low-melting point metal 16 with high precision by the thickness of the second substrate 13 so that as a result, it may be possible to easily obtain a blowout characteristic.

Figure 4:
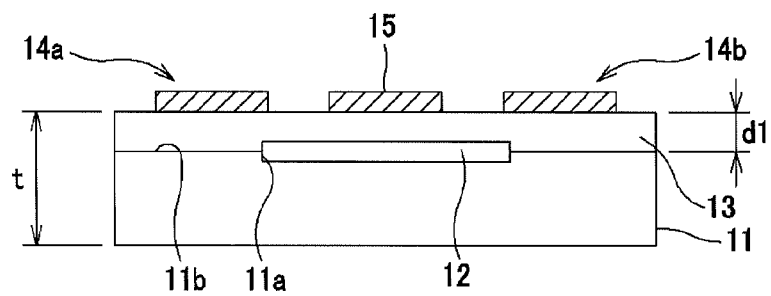
FIG. 4 is a view for describing a change in a blowout time when a distance d1 between a heating body and a heating body electrode is changed according to one or more embodiments of the present invention.

For example, Table 1 shows a change in a blowout time when a distance d1 between the heating body 12 and the heating body electrode 15 is changed as shown in FIG. 4. In this case, as prerequisites, the entire thickness t of the substrate 11 and the second substrate 13 is set to 200 μm and by using the heating body 12 having an electric power consumption of 4 W, the distance d1 is changed from 20 μm to 200 μm.

TABLE 1

| d1[μm] | 20 | 50 | 100 | 150 | 200 |
|---|---|---|---|---|---|
| Blowout time [sec] | 5 | 9 | 15 | 30 | 39 |

As clearly indicated by Table 1, as the distance d1 between the heating body 12 and the heating body electrode 15 becomes smaller, a better blowout characteristic can be obtained. Based upon the results, to obtain a good blowout characteristic, it may be advantageous to adjust the distance d1 with high precision. The protective element 1 relating to the structural body 1a may make it possible to adjust the positions of the heating body 12 and the low-melting point metal 16 with high precision by the thickness of the second substrate 13, and consequently to easily obtain a better blowout characteristic.

Figure 5:
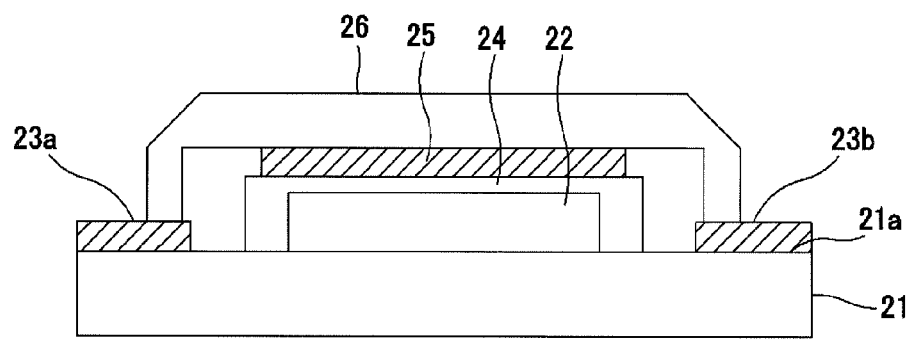
FIG. 5 is a view for describing a configuration of a protective element and a comparative example according to one or more embodiments of the present invention.

Moreover, in the protective element 1 relating to the structural body 1a, because the heating electrode 15 is kept so as not to protrude in the thickness direction of the substrate 11, that is, in the z-axis direction, relative to the first electrode 14a and the second electrode 14b, the shape of the low-melting point metal 26 is prevented from being formed into a convex shape relative to the substrate 21, for example, as in the case of the protective element 2 relating to a comparative example shown in FIG. 5; therefore, even in the case when it is heated and allowed to flow, the flux is not interrupted.

The protective element 2 relating to the comparative example shown in FIG. 5 is manufactured in the following manner. First, a heating body 22, a first electrode 23a and a second electrode 23b are layered on the same plane 21a of a substrate 21. Then, a second insulating member 24 is layered thereon so as to cover only the heating body 22 among the heating body 22, the first electrode 23a and the second electrode 23b layered on the same plane 21a of the substrate 21. Moreover, on the second insulating member 24, a heating body electrode 25 to be electrically connected to the heating body 22 is layered so as to be superimposed on the heating body 22. Furthermore, a low-melting point metal 26 is layered over the first electrode 23a to the second electrode 23b from the heating body electrode 25.

In the case of the protective element 2 manufactured in this manner, because the shape of the low-melting point metal 26 is formed into a convex shape, upon being heated and allowed to flow, its flux is interrupted because of the following reasons.

Referring to FIG. 6, an explanation will be given to blowout characteristic of a low-melting point metal about the protective element 1 according to one or more embodiments of the present invention and the protective element 2 relating to the comparative example.

Figure 6A:
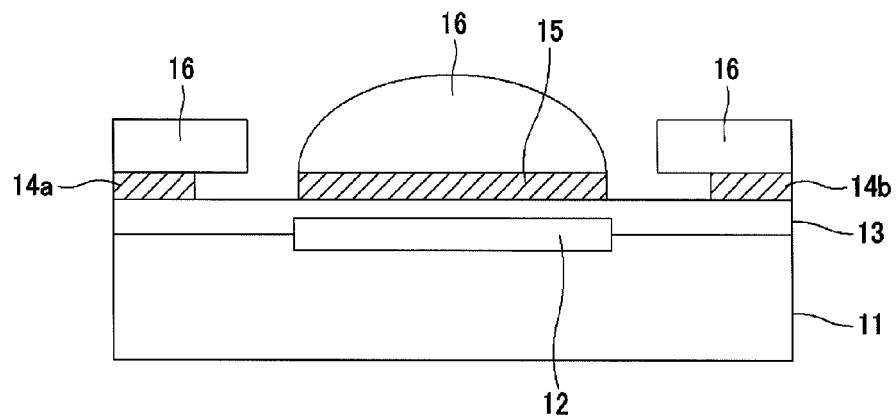
FIG. 6(A) and FIG. 6(B) are views for describing a blowout characteristic of a low-melting point metal in a protective element as well as a protective element and a comparative example according to one or more embodiments of the present invention.

In one or more embodiments, the case of the protective element 1, when the low-melting point metal 16 is heated to fuse, the low-melting point metal 16 is drawn into the respective electrodes, as shown in FIG. 6(A), and in particular, more low-melting point metal 16 is drawn into the vicinity of the heating body electrode 15 near the heating body 12. In this case, because the heating body electrode 15 in the protective element 1 is kept so as not to protrude to the first electrode 14*a* and the second electrode 14*b*, more low-melting point metal 16 can be easily drawn into the heating body electrode 15.

Figure 6B:
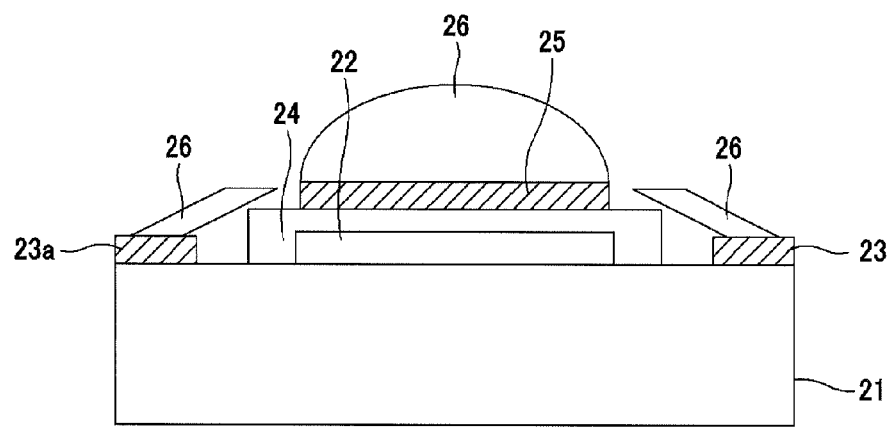

In contrast, in the case of the protective element 2, when the low-melting point metal 26 is heated to fuse, as shown in FIG. 6(B), a flowing force of the low-melting point metal 26 is exerted toward the first electrode 23*a* and the second electrode 23*b* located at a position lower than the heating body electrode 25 due to the gravity, with the result that the flowability of the low-melting point metal 26 of a portion to be drawn into the heating body electrode 25 is interrupted.

In this manner, the protective element 1 according to one or more embodiments may make it possible to prevent the low-melting point metal 16 from being formed into a convex shape, and because upon being heated and allowed to flow, the flux is not interrupted, it may be possible to carry out a reliable blowout of the low-melting point metal 16 on the current path quickly.

Moreover, in the protective element 1 according to one or more embodiments as shown in FIG. 7(A) and the protective element 2 relating to the comparative example shown in FIG. 7(B), in the case when the thicknesses from the electrodes having the highest position to the uppermost portions 17*a*, 27*a* of the cap 17, 27 covering the low-melting point metals, not shown, are set to the same thickness, the thicknesses from the lower portion of the substrate 11, 21 to the electrodes having the highest position (hereinafter, referred to as "substrate thickness d2") can be made thinner in the protective element 1 according to one or more embodiments, in comparison with the protective element 2 relating to the comparative example, as shown in FIGS. 7(A) and 7(B). As a result, the protective element 1 according to one or more embodiments may make it possible to reduce the entire thickness (hereinafter, referred to as "product entire thickness d3") of the product itself in comparison with the protective element 2 relating to the comparative example.

Figure 8A:
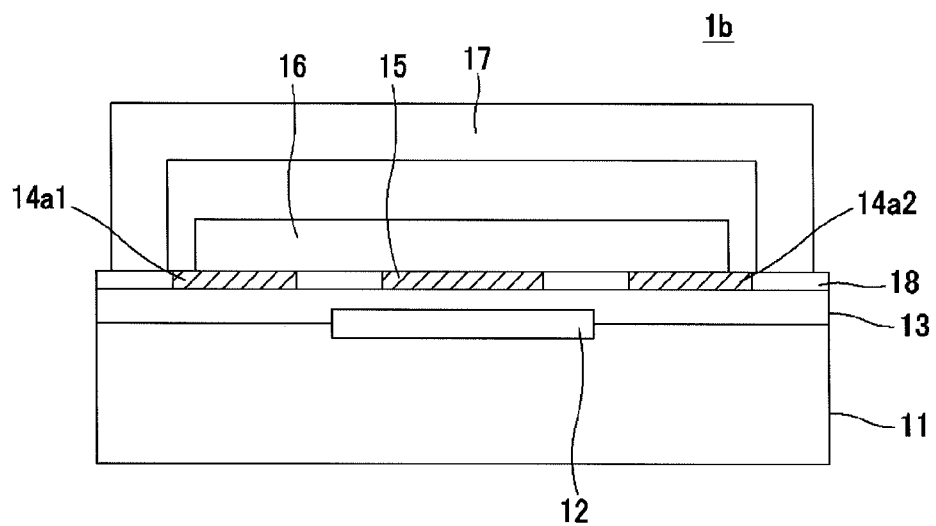
FIG. 8(A) and FIG. 8(B) are views for describing a specific structure of a protective element according to one or more embodiments of the present invention.

Moreover, the protective element 1 may have a structural body 1*b* according to one or more embodiments of the present invention, as shown in FIG. 8(A), in which a third substrate 18 is layered on a gap between the respective electrodes on the second substrate 13 as well as on the outer peripheral portion thereof. The third substrate 18 may be position-adjusted so that the upper surfaces of the first electrodes 14*a*1, the second electrode 14*a*2 and the heating body electrode 15 can respectively have planes having the same level.

Figure 8B:
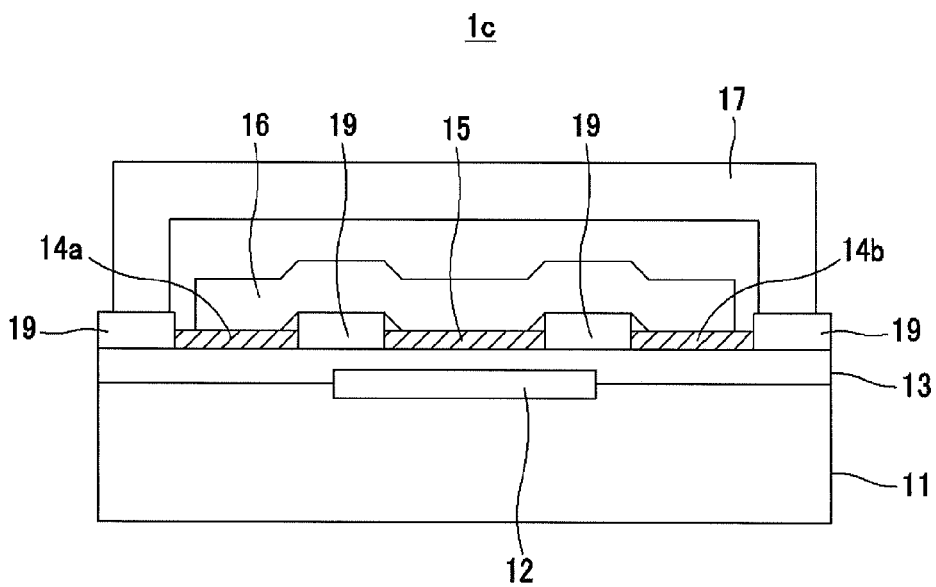

Furthermore, the protective element 1 may have a structural body 1*c* relating to a modified example, as shown in FIG. 8(B), in which a fourth substrate 19 is layered on a gap between the respective electrodes on the second substrate 13 as well as on the outer peripheral portion thereof. The fourth substrate 19 has its upper surface raised to a position higher than the respective electrodes, that is, the first electrode 14*a*, the second electrode 14*b* and the heating body electrode 15. Therefore, upon causing a blowout of the low-melting point metal 16, the structural body 1*c* may make it possible to prevent the low-melting point metal 16 from remaining among the electrodes, thereby it may be possible to positively carry out a reliable blowout of the current path by heating the heating body 12.

Figure 9A:
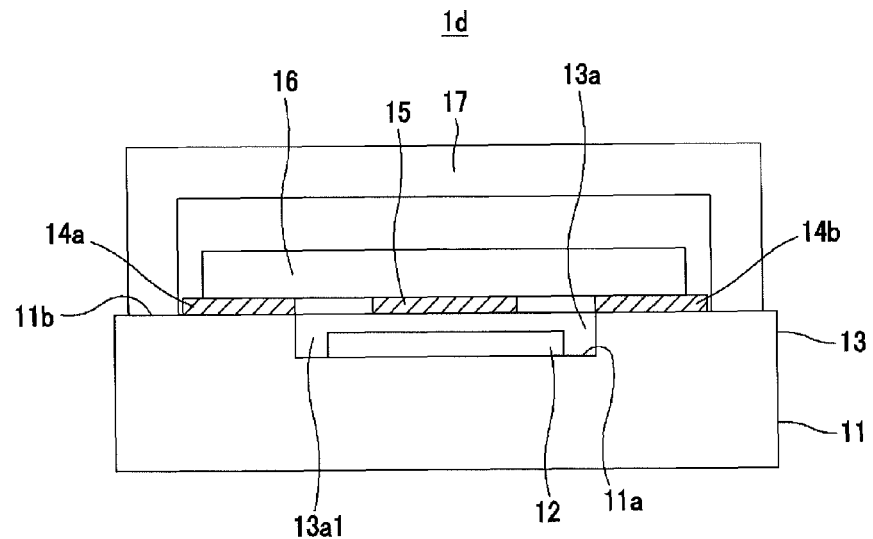
FIG. 9(A) and FIG. 9(B) are views for describing a specific structure of a protective element according to one or more embodiments of the present invention.

The protective element 1 may have a configuration as a structural body 1*d* relating to a second embodiment in which, as shown in FIG. 9(A), a concave portion 11*a* capable of embedding the heating body 12 therein is formed in the center of the substrate 11, and the heating body 12 embedded in the concave portion 11*a* is coated with a second insulating member 13*a*1 by using, for example, a printing process, so that the upper surface 11*b* of the substrate 11 and the upper surface 13*a* of the second insulating member 13*a*1 can respectively have planes having the same level. In this case, in the structural body 1*d*, by stacking the heating body electrode 15 on the upper surface 13*a* of the second insulating member 13*a*1, the height of the heating body electrode 15 in the thickness direction of the substrate 11 can be set to the same height as that of the first electrode 14*a* and the second electrode 14*b*, in the same manner as in the structural bodies 1*a* to 1*c*. Moreover, in the structural body 1*d*, the shape of the low-melting point metal 16 is formed into a flat plate shape, and the connection reliability to each of the electrodes before blowout is consequently enhanced so that it may be possible to positively carry out a blowout between the electrodes quickly at the time of a blowout process.

Figure 9B:
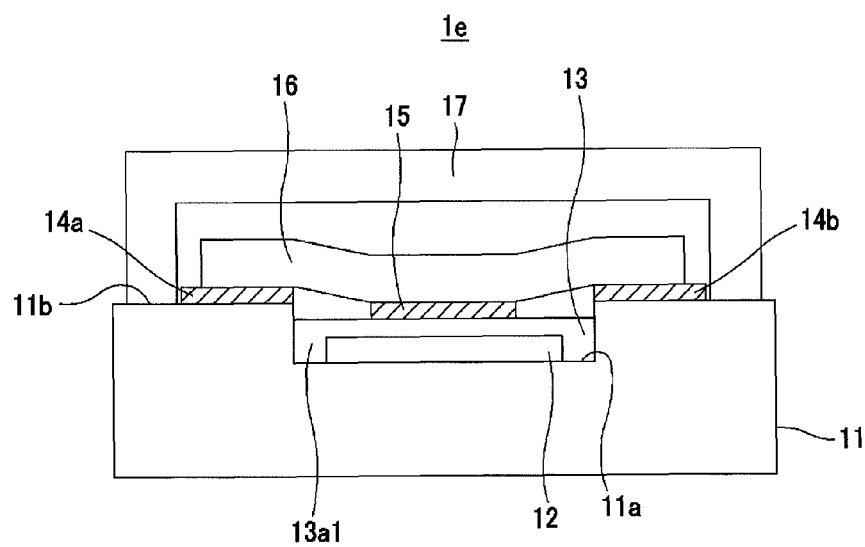

Moreover, the protective element 1 may have a configuration as a structural body 1*e* relating to the second embodiment in which, as shown in FIG. 9(B), a concave portion 11*a* capable of embedding the heating body 12 therein is formed in the center of the substrate 11, and in the concave portion 11*a*, the heating body 12 and a second insulating member 13*a*1, which covers the entire heating body 12, may be embedded by using, for example, a printing process. With respect to this structural body 1*e*, by stacking the heating body electrode 15 on the second insulating member 13*a*1, the height of the heating body electrode 15 in the thickness direction of the substrate 11 can be made lower than the height of the first electrode 14*a* and the second electrode 14*b*. Moreover, in the structural body 1*e*, the shape of the low-melting point metal 16 is formed into a concave shape in accordance with the height of the heating body electrode 15, and as clearly indicated by performance evaluations to be described later, it may be possible to positively carry out a blowout between the electrodes quickly at the time of a blowout process.

In this manner, in the structural body 1*e*, by disposing the heating body electrode 15 in the thickness direction of the substrate 11 so as to have a height lower than the height of the first electrode 14*a* and the second electrode 14*b*, it may be possible to achieve a particularly good blowout characteristic.

For example, as shown in FIG. 10, the heights of the first electrodes 14*a*, 23*a* and the second electrodes 14*b*, 23*b* are kept constant, and when the difference in heights (hereinafter, referred to as "electrode step difference d4") of the heating body electrodes 15, 25 is varied based upon the above mentioned height as the standard, the blowout time relative to the electrode step difference d4 is indicated by the following Table 2.

In this case, the substrate thickness specified by the z-axis direction of the substrates 11, 21 was set to 500 μm and the substrate thickness specified by the z-axis direction of the second insulating members 13*a*1, 24 was set to 200 μm, and by using the heating bodies 12, 22 having an electric power consumption of 4 W, the distance d2 was varied in a range from −200 μm to 300 μm.

Figure 10A:
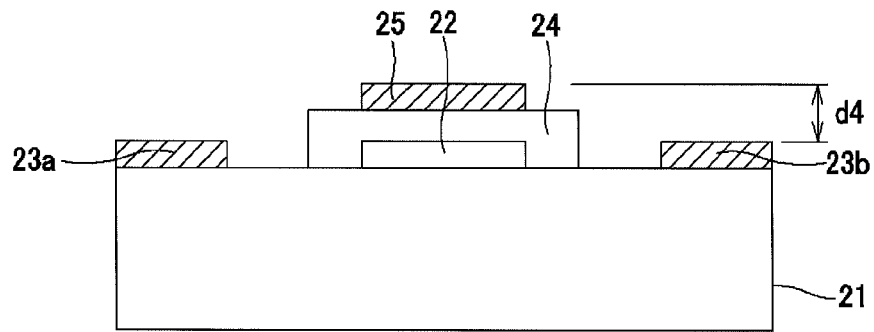
FIG. 10(A), FIG. 10(B) and FIG. 10(C) are views for describing a change in a blowout time in the case when an electrode step difference d4 is changed according to one or more embodiments of the present invention.
Figure 10B:
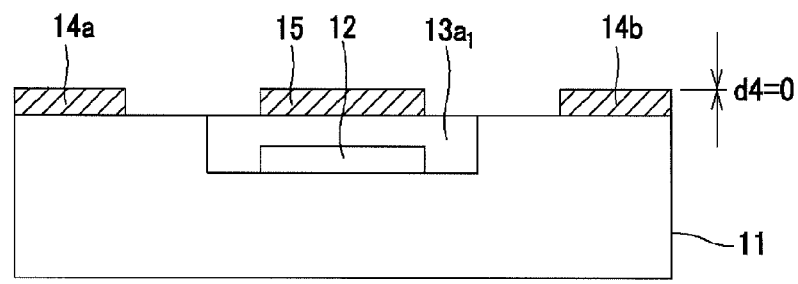
Figure 10C:
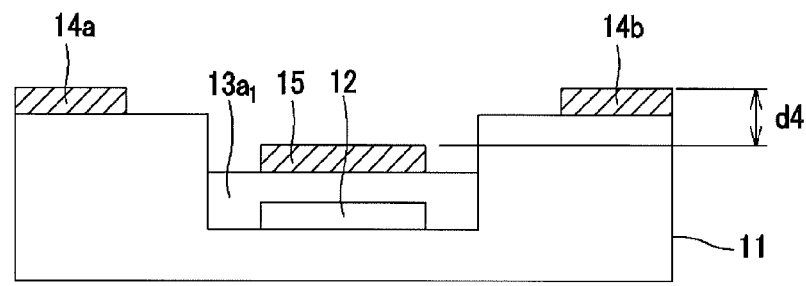

FIG. 10(A) shows a state in which the electrode step difference is a positive value. That is, this drawing shows the structural body of the protective element 2 of the comparative example. FIG. 10(B) shows a state in which the electrode step difference is 0. That is, this drawing shows the structural body 1*d*. FIG. 10(C) shows a state in which the electrode step difference is a negative value. That is, this drawing shows the structural body 1*e*.

TABLE 2

| | d4 [μm] | | | | | | |
|---|---|---|---|---|---|---|---|
| | −200 | −100 | −50 | 0 | 50 | 100 | 200 | 300 |
| Blowout time [sec] | 7.7 | 8 | 8.1 | 9 | 11 | 15 | 32 | No blowout |

As clearly indicated by the above Table, as the electrode step difference d4 becomes a smaller value, the blowout time becomes shorter. This is because the fused low-melting point metal becomes more easily drawn into the heating body electrode due to gravity.

In this manner, in the protective element 1 according to one or more embodiments, by adopting the structures of the structural bodies 1*d*, 1*e*, the height of the heating body electrode 15 in the thickness direction of the substrate 11 is set the same or lower than the height of the first electrode 14*a* and the second electrode 14*b* so that it may be possible to achieve a good blowout characteristic. In one or more embodiments, in the protective element 1, by setting the height of the heating body electrode 15 in the thickness direction of the substrate 11 to be lower than the height of the first electrode 14*a* and the second electrode 14*b*, it may be possible to achieve a better blowout characteristic.

Figure 11:
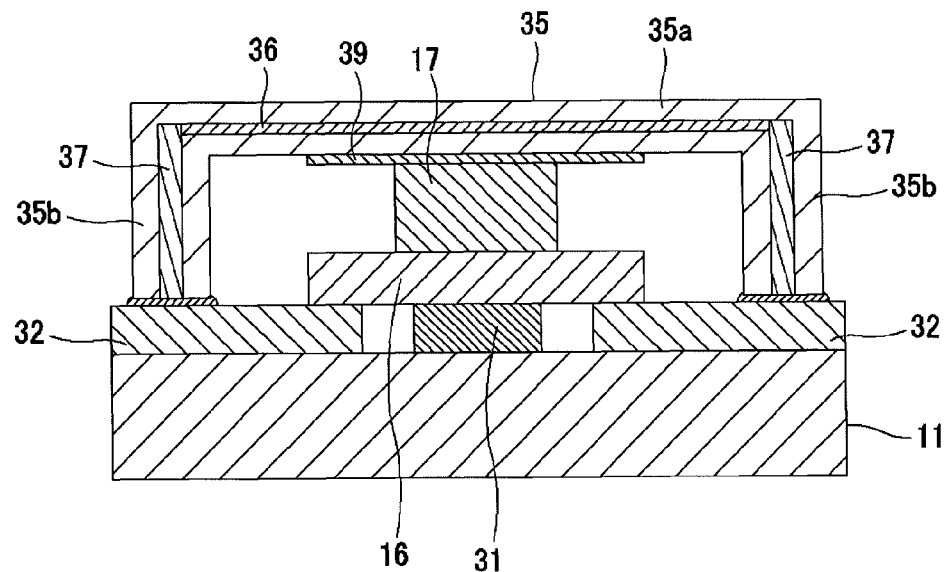
FIG. 11 is a view for describing a modified example of a protective element according to one or more embodiments of the present invention.
Figure 12:
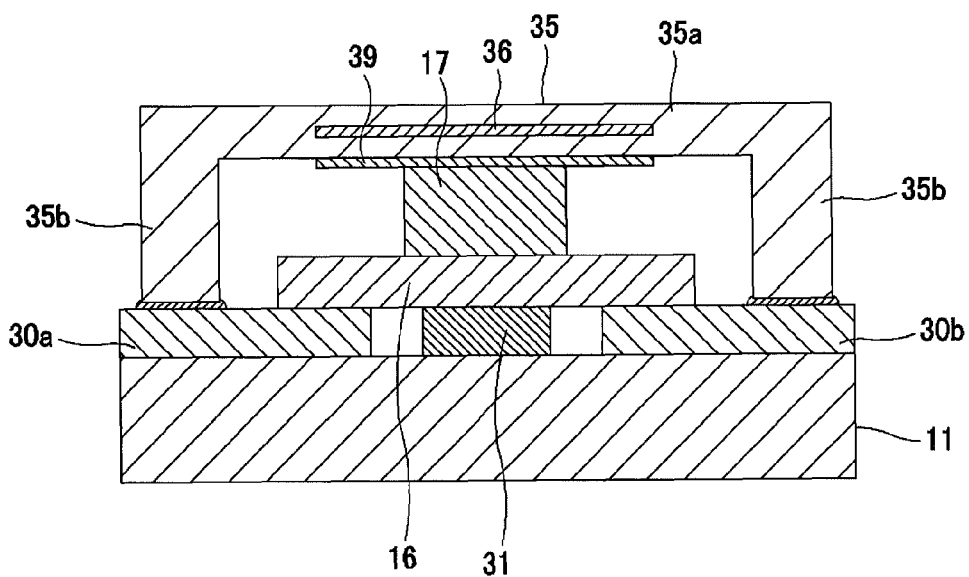
FIG. 12 is a view for describing a modified example of a protective element according to one or more embodiments of the present invention.

Moreover, in one or more embodiments, in addition to the formation of the heating body 12 in the concave portion 11*b* of the substrate 11, a heating body may be formed on a cap, as shown in FIG. 11 and FIG. 12. In this structural body 1*f*, without installing the heating body on the substrate side 11, by using a heating body 36 formed on a cap 35, the low-melting point metal 16 is blown out. The structural body 1*f* has a configuration in which, on a rectangular-shaped substrate 11 made of an insulating member, first and second electrodes 30*a*, 30*b*, a substrate electrode 31 layered between the first and second electrodes 30*a*, 30*b*, a low-melting point metal 16 layered from the substrate 31 toward the first and second electrode to cause a blowout of the current path between the first electrode 30*a* and the second electrode 30*b* by heating, and a pair of heating body electrodes 32, 32 electrically connected to the heating body 36, with a conductive layer 37 formed on the cap 35 interposed therebetween, are installed.

The first electrode 30*a* and the second electrode 30*b* are made of, for example, W, Mo, Ag, Pt, Pd, Sn, Au, Cu or the like, and when embedded in the above-mentioned charging and discharging control circuit 120, are connected onto the charging and discharging current path. Moreover, the substrate electrode 31 may be formed by using the same material as that of the first and second electrodes 30*a*, 30*b*, and formed on the substrate 11 by a batch process together with the first and second electrodes 30*a*, 30*b*.

Onto these first and second electrodes 30*a*, 30*b* and the substrate electrode 31, the low-melting point metal 16 is connected.

Moreover, the structural body 1*f* is provided with the cap 35 that covers the surface of the substrate 11. The cap 35 is formed by using a member having an insulating property, such as, for example, a ceramic substrate, a glass epoxy substrate or the like, in the same manner as in the substrate 11.

Moreover, the cap 35 has a ceiling surface portion 35*a* on which the heating body 36 is provided, and a side wall 35*b* on which a conductive layer 37 electrically connected to the heating body 36 is provided.

The conductive layer 37 may be formed by using a known conductive material, such as, for example, Cu, W, Mo, Au or the like. Moreover, the conductive layer 37 is made to face outward from an end face of the bottom end portion of the side wall 35*b*. Moreover, the side wall 35*b* has its base end portion connected to the heating body electrodes 32, 32 by using an adhesive agent 38 having conductivity, such as a conductive adhesive paste, a solder paste or the like. Thus, the side wall 35*b* has its conductive layer 37 electrically connected to the heating electrodes 32, 32.

On the ceiling surface portion 35*a*, the heating body 36 is formed along a gap relative to the side wall 35*b*. In the same manner as in the heating body 12, the heating body 36 is a conductive member having a comparatively high resistance value, which generates heat when energized, and is made of, for example, W, Mo, Ru or the like. The heating body 36 is formed by processes in which a powder of an alloy or a composition, a compound of these metals is mixed with a resin binder or the like, to form a paste, and this paste is formed as a pattern on the ceiling surface portion 35*a* by using a screen printing technique, and subjected to a baking process or the like. After the heating body 36 has been formed on the ceiling surface portion 35*a*, an insulating member forming the cap 35 is further layered thereon so that the heating body 36 is built into the ceiling surface portion 35*a*. Moreover, the heating body 36 is formed at a position facing the low-melting point metal 16 when the cap 35 covers over the substrate 11.

Moreover, the heating body 36 has its two connected to the conductive layer 37 formed on the side wall 35*b*. Furthermore, the ceiling surface portion 35*a* is allowed to generate heat when the heating body 36 is energized through the heating body electrodes 32, 32 and the conductive layer 37. Therefore, the structural body 1*f* may make it possible to heat the low-melting point metal 16 from the ceiling surface portion 35*a* side.

Moreover, the ceiling surface portion 35*a* may be provided with a cap electrode 39 formed on the inner surface that is made face to face with the low-melting point metal 16. The cap electrode 39 is formed at a position that is superimposed with the heating body 36. When the heating body 36 generates heat so that the low-melting point metal 16 is fused, the cap electrode 39 is made in contact with the fused conductor to allow the fused conductor to be wet and expanded thereon so that the permissible amount for holding the fused conductor can be increased. In this case, the structural body 1*f* has its cap electrode 39 heated by the heating body 36 so that the fused conductor is positively wet and expanded on the cap electrode 39, it may be possible to prevent short circuit caused by overflowed fused conductor.

In the structural body 1*f* of this type, because no heating body is formed on the substrate 11, the heights in the thickness direction of the substrate 11 between the first and second electrodes 30*a*, 30*b* to be formed on the same surface of the substrate 11 and the substrate electrode 31 can be formed into the same level. Therefore, in the structural body 1*f* also, as a result, it may be possible to easily obtain a good blowout characteristic.

Additionally, in the structural body 1*f* also, as described earlier, a configuration may be prepared in which a concave portion 11*a* is formed in the center of the substrate 11, and by forming the substrate electrode 31 in the concave portion 11*a*, the height in the thickness direction of the substrate 11 of the substrate electrode 31 may be made lower than the heights of the first and second electrodes 30a, 30b. Thus, the structural body 1f is designed such that the shape of the low-melting point metal 16 is formed into a concave shape in accordance with the height of the substrate electrode 31, and as clearly indicated by performance evaluations as described earlier, it may be possible to positively carry out a blowout between the electrodes quickly at the time of a blowout process.

In this manner, in the structural body 1f, by setting the height in the thickness direction of the substrate 11 of the substrate electrode 31 to the same height as the height of the first electrode 30a and the second electrode 30b or to a height lower than the height thereof, it may be possible to obtain, in particular, a good blowout characteristic.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

REFERENCE SIGNS LIST 1, 2 . . . protective element,
1a-1e . . . structural body,
11, 21 . . . substrate,
11a . . . concave portion,
11b . . . surface,
12, 22, 36 . . . heating body,
13 . . . second substrate,
13a . . . upper surface,
13a1, 24 . . . second insulating member,
14a, 23a . . . first electrode,
14b, 23b . . . second electrode,
15, 25, 32 . . . heating body electrode,
16, 26 . . . low-melting point metal,
17, 35 . . . cap,
17a . . . uppermost portion,
18 . . . third substrate,
19 . . . fourth substrate,
21a . . . plane,
37 . . . conductive layer,
38 . . . adhesive agent,
39 . . . cap electrode,
100 . . . buttery module,
100a . . . positive electrode terminal,
100b . . . negative electrode terminal,
101, 102 . . . fuse,
103 . . . resistor,
110 . . . battery,
111-114 . . . battery cell,
120 . . . charging and discharging control circuit,
121 . . . current control element,
123 . . . control unit,
140 . . . detection circuit,
150 . . . current control element,
151 . . . through hole,
152 . . . connection terminal,
200 . . . charging device

The invention claimed is:

1. A protective element comprising:
a substrate comprising a first insulating member and a concave portion;
a heating body layered on the concave portion of the substrate;
a second insulating member layered on the substrate covering the heating body;
first and second electrodes layered on a surface of the substrate on which the second insulating member is layered;
a heating body electrode layered on the second insulating member superimposed with the heating body, and electrically connected to a current path between the first and the second electrodes and the heating body; and
a low-melting point metal layered between the heating body electrode and the first and the second electrodes so as to cause a blowout of the current path between the first and the second electrodes by heating,
wherein the heating body electrode is disposed at a same or lower position in a thickness direction of the substrate relative to the first and the second electrodes.

2. The protective element according to claim 1, wherein the heating body and the second insulating member are embedded into the concave portion formed on the substrate.

3. The protective element according to claim 1, wherein the heating body is disposed at a lower position relative to the first and the second electrodes in the thickness direction of the substrate.

4. The protective element according to claim 3, wherein the second insulating member comprises a member having a thermal conductivity higher than that of the first insulating member.

5. A method for manufacturing a protective element comprising:
stacking a heating body in a concave portion formed on a substrate comprising a first insulating member;
stacking a second insulating member on the substrate covering the heating body;
stacking first and second electrodes on a surface of the substrate on which the second insulating member is stacked;
stacking a heating body electrode on the second insulating member so as to be superimposed with the heating body, the heating body electrode electrically connected to a current path between the first and the second electrodes and the heating body; and
stacking, from the heating body electrode to the first and the second electrodes, a low-melting point metal so as to cause a blowout of the current path between the first and the second electrodes by heating,
wherein the heating body electrode is disposed at a same or lower position in a thickness direction of the substrate relative to the first and the second electrodes.

6. A battery module comprising:
a battery comprising one or more battery cells;
a charging and discharging control circuit connected to the battery in series to control charging and discharging of the battery;
a protective element connected to a charging and discharging current path between the battery and the charging and discharging control circuit;
a detection circuit for detecting a voltage value of each of the one or more battery cells of the battery; and
a current control element for controlling an electric current flowing through the protective element, the protective element further comprising:
a substrate comprising a first insulating member and a concave portion;
a heating body layered on the concave portion of the substrate;
a second insulating member layered on the substrate covering the heating body;

first and second electrodes layered on a surface of the substrate on which the second insulating member is layered and connected to the charging and discharging current path, a heating body electrode layered on the second insulating member superimposed with the heating body and electrically connected to a current path between the first and the second electrodes and the heating body; and a low-melting point metal layered between the heating body electrode and the first and the second electrodes so as to cause a blowout of a current path between the first and the second electrodes by heating, wherein the heating body electrode is disposed at a same or lower position in a thickness direction of the substrate relative to the first and second electrodes, and wherein the current control element carries out a controlling process such that when a voltage value of each of the one or more battery cells detected by the detection circuit is of not within a predetermined range, a current is allowed to flow from the heating body electrode to the heating body.

7. A protective element comprising:

a substrate comprising an insulating member;

first and second electrodes layered on a surface of the substrate;

a substrate electrode layered between the first and the second electrodes on the surface of the substrate;

a low-melting point metal layered between the substrate electrode and the first and the second electrodes so as to cause a blowout of a current path between the first and the second electrodes by heating, a cap covering the surface of the substrate;

a heating body formed on a ceiling surface portion of the cap; and a heating body electrode layered on the surface of the substrate and electrically connected to the heating body through a conductive layer formed on the cap, wherein the substrate electrode is disposed at a same or lower position in a thickness direction of the substrate relative to the first and the second electrodes.

8. A battery module comprising:

a battery comprising one or more battery cells;

a charging and discharging control circuit connected to the battery in series to control charging and discharging of the battery;

a protective element connected to a charging and discharging current path between the battery and the charging and discharging control circuit;

a detection circuit for detecting a voltage value of each of the one or more battery cells;

a current control element for controlling an electric current flowing through the protective element, the protective element comprising:

a substrate comprising an insulating member;

first and second electrodes layered on a surface of the substrate;

a substrate electrode layered between the first and the second electrodes on the surface of the substrate;

a low-melting point metal layered between the substrate electrode and the first and the second electrodes so as to cause a blowout of a current path between the first and the second electrodes by heating, a cap covering the surface of the substrate;

a heating body formed on a ceiling surface portion of the cap; and a heating body electrode layered on the surface of the substrate and electrically connected to the heating body through a conductive layer formed on the cap, wherein the substrate electrode is disposed at a same or lower position in a thickness direction of the substrate relative to the first and the second electrodes, and wherein the current control element carries out a controlling process such that when a voltage value of each of the one or more battery cells detected by the detection circuit is not within a predetermined range, a current is allowed to flow from the heating body electrode to the heating body.

* * * * *